United States Patent [19]

Miller et al.

[11] 4,108,896

[45] Aug. 22, 1978

[54] ANTHRACENE DERIVATIVES

[75] Inventors: Laird F. Miller, Loveland, Ohio; Robert W. Fleming, Ann Arbor, Mich.

[73] Assignee: Richardson-Merrell Inc., Wilton, Conn.

[21] Appl. No.: 317,247

[22] Filed: Dec. 21, 1972

[51] Int. Cl.² ............................................. C07C 97/10
[52] U.S. Cl. ......................... 260/570.5 C; 260/293.62; 260/326.81; 260/343.7; 260/501.18; 260/501.19; 424/248.57; 424/267; 424/274; 424/280; 424/316; 424/330; 544/79
[58] Field of Search .................... 260/570.5 C, 501.18, 260/501.19, 343.7, 293, 294.3, 326.81; 424/330; 544/79

[56] References Cited

U.S. PATENT DOCUMENTS

| 3,465,039 | 9/1969 | Siemer | 260/570.5 X |
| 3,626,011 | 12/1971 | Bordenca et al. | 260/570.7 X |

Primary Examiner—Robert V. Hines
Attorney, Agent, or Firm—William J. Stein; Eugene O. Retter; George W. Rauchfuss, Jr.

[57] ABSTRACT

Novel 1,5 and 1,8-bis-basic ketones of anthracene useful for the prevention and inhibition of viral infections are prepared by reacting 1,5 and 1,8 bis(ω-haloacyl)anthracenes with a secondary amine.

5 Claims, No Drawings

ANTHRACENE DERIVATIVES

FIELD OF THE INVENTION

This invention relates to new organic chemical compounds, to their preparation, and to pharmaceutical compositions containing such compounds. The compounds described herein are antiviral agents which are useful in inactivating or inhibiting viruses by their administration to either an infected or a non-infected host.

BACKGROUND OF THE INVENTION

There is a growing body of information that viruses play a vital role in a broad range of diseases, some of which represent the most serious of man's ills. Arthritis, juvenile arthritis, diabetes, Hodgkin's disease and various immunological diseases and degenerative diseases of the central nervous system have been linked to viruses as the causative agents.

At present, the control of virus infections is primarily achieved by means of immunization vaccines. For example, poliomyelitis, smallpox, measles and influenza are well recognized diseases in which viral vaccines have proven effective. In general, however, viral vaccines have had only a moderate success in animal prophylaxis. Each vaccine acts primarily against a specific virus and is not heterophilic in the protection it offers. Hence, vaccines have not provided a practical solution against the wide array of infectious viruses, even when limited as for example, solely to respiratory viruses.

One approach to the control of virus-related diseases and, particularly to the spread of such virus diseases, has been to search for medicinal agents or chemotherapeutic agents which are capable of inhibiting the growth of viruses, thereby preventing the spread of disease as well as preventing further damage to cells and tissues of the animal host which have not as yet been infected. Heretofore, only a limited number of virus infections such as smallpox, Asian influenza and herpes keratitis have been prevented by chemical antiviral agents. Sulfonamides and antibiotics which have revolutionized the treatment of bacterial infections have substantially no effect upon virus infections. Certain infections caused by large viruses, such as lymphogranuloma venereum, psittacosis and trachoma have been successfully treated using antibiotics and sulfa drugs. However, the majority of infections have not been responsive to attack by chemotherapeutic agents. Thus, it can be seen that there is a need for new chemotherapeutic agents which are effective against a broad range of virus diseases, and which at the same time, are non-toxic to the host.

As a result of a long series of investigations, applicants have discovered a novel class of 1,5 and 1,8-bis-basic ketones of anthracene which are particularly useful as antiviral agents. These compounds are effective against a wide spectrum of virus infections and are useful in treating such infections both prophylactically and therapeutically. Copending application, Ser. No. 23,468, filed Mar. 27, 1970, whose counterpart has been published as Belgium Pat. No. 764,870, represents the closest art known to applicants and discloses ketones of fluorene useful as antiviral agents. The bis-basic ketones of the present invention, however, are derived from a totally different and non-related 6,6,6 membered, fully aromatic, anthracene ring system, which bears little, if any, relationship to the 6,5,6 membered fluorene ring system.

To applicants' knowledge the compounds described and claimed herein are novel compounds which have not previously been described nor reported in the literature. The instant compounds possess a wide spectrum of antiviral activity in varying degrees which could not have been predicted from a knowledge of the present state of the art.

SUMMARY OF THE INVENTION

This invention relates to new derivatives of anthracene, to their preparation, compositions thereof and to their use as pharmaceutical agents. More particularly, the compounds of the present invention relate to 1,5 or 1,8-bis-basic ketones of anthracene, which are useful as antiviral agents. Still more particularly, the compounds of the present invention may be represented by the following general formula:

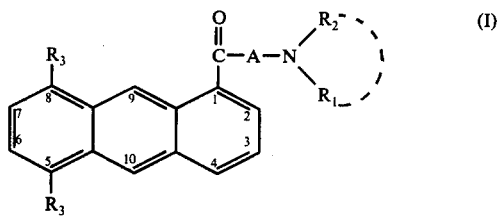

wherein A is a straight or branched alkylene chain having from 1 to 6 carbon atoms; $R_1$ and $R_2$ are each selected from the group consisting of hydrogen, lower alkyl having from 1 to 6 carbon atoms, cycloalkyl having from 3 to 6 carbon atoms, alkenyl having from 3 to 6 carbon atoms in which the unsaturation is in a position other than in the 1-position of the alkenyl group, and when $R_1$ and $R_2$ are taken together with the nitrogen atom to which they are attached, represent the pyrrolidinyl, piperidino or morpholino radical; $R_3$ is selected from the group consisting of hydrogen and the radical,

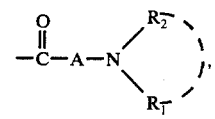

with the proviso that one and only one such $R_3$ group is hydrogen; and the pharmaceutically acceptable acid addition salts thereof.

The compounds within the scope of the present invention include both the free base form as well as the pharmaceutically acceptable acid addition salts thereof. In general, the salts of these compounds are crystalline materials which are soluble in water and various hydrophilic organic solvents, and which, in comparison to their free base forms, demonstrate higher melting points and an increased stability.

The compounds of the present invention can be readily prepared by reacting a bis-ω-haloalkanoyl anthracene with a secondary amine as illustrated by the following reaction scheme:

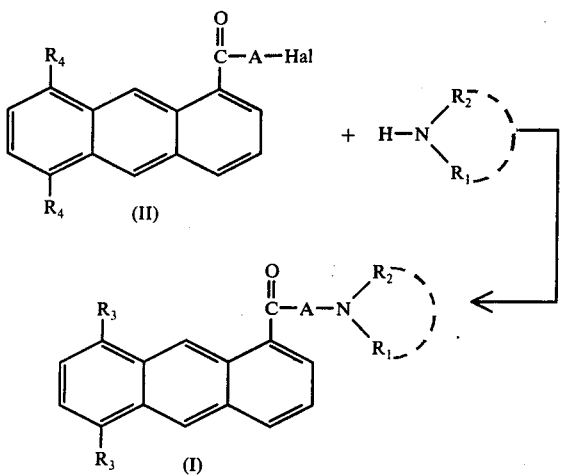

In the above reaction $R_4$ is either hydrogen or the radical

with the proviso that one and only one such $R_4$ group is hydrogen; Hal is selected from the group consisting of chlorine, bromine and iodine; and the symbols A, $R_1$, $R_2$ and $R_3$ have the values previously assigned to them.

To achieve an antiviral effect the compounds of this invention are administered to a suitable host using a variety of compositions. Such compositions may be administered either prior to infection, as a prophylactic use or treatment, or they may be therapeutically administered subsequent to infection of the host as a curative use or treatment.

A wide variety of compositions are within the scope of the present invention. Thus, the instant compounds may be applied externally or topically directly at the situs of the infection, or they may be administered internally or systemically, irrespective of whether the treatment is prophylactic or curative in nature. In either event, replication of the virus is inhibited or prevented with the concomitant result that the various disease symptoms characteristic of the pathogenic virus infection are no longer present.

DETAILED DESCRIPTION OF THE INVENTION

As can be seen from general formula (I) above, each basic ketone side chain substituted on the anthracene nucleus can be viewed as consisting of a ketonic bridge located at one end of the chain, a basic amino group located at the opposite or terminal end, with an alkylene chain of determinate length separating both functional groups. Additionally, each of the side chains is located on a terminal ring of the anthracene nucleus.

The basic amino group is a primary, secondary or tertiary amino group. Each $R_1$ and $R_2$ can be hydrogen or a lower alkyl group. The term lower alkyl as applied to this basic amino group relates to groups having from 1 to 6 carbon atoms. Illustrative of such groups are straight or branched chain alkyl groups as for example: methyl, ethyl, n-propyl, isopropyl, n-butyl, sec-butyl, tert-butyl, isoamyl, n-pentyl and n-hexyl.

Each $R_1$ and $R_2$ can also represent a cycloalkyl group containing from 3 to 6 carbon atoms. Such groups include the cyclopropyl, cyclobutyl, cyclopentyl and cyclohexyl radicals.

The symbols $R_1$ and $R_2$ also represent an alkenyl group, having from 3 to 6 carbon atoms. In addition, the unsaturation present in this group must be in a position other than the 1-position inasmuch as any unsaturation at this point is readily hydrolyzable. Illustrative of such groups are the allyl, 3-butenyl and the 4-hexenyl radicals.

$R_1$ and $R_2$ also represent various saturated, monocyclic, heterocyclic radicals when taken in conjunction with the amino nitrogen atom to which $R_1$ and $R_2$ is attached. Typical of such heterocyclic groups are the pyrrolidinyl, piperidino and morpholino radicals. Compounds containing such groups are readily prepared and typify saturated, monocyclic, heterocyclic radicals which are generally useful in lieu of the dilower alkylamino groups present in the compounds of this invention.

Each of the alkylene groups represented by the symbol A in general formula (I) above is an alkylene group having from 1 to 6 carbon atoms and can be either a straight or a branched alkylene chain. Additionally, each of the alkylene groups can be different; preferably, however, both alkylene groups are the same. Illustrative of such alkylene groups are ethylene, propylene, 1,3-propylene, butylene, 1,4-butylene, pentamethylene, 3-methyl-1,5-pentylene and hexamethylene.

It is also apparent from general formula (I) and its description that the compounds of the present invention include structures in which $R_3$ represents a hydrogen atom in the 8-position of the anthracene nucleus and the 5-position contains the radical

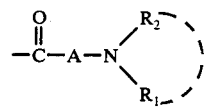

as more fully illustrated by the following general formula:

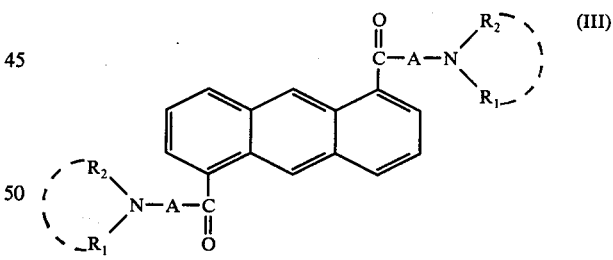

wherein the symbols A, $R_1$ and $R_2$ have the values previously assigned. Illustrative of the base compounds of this invention represented by formula (III) are: 1,5-bis [3-(N,N-dihexylamino)propionyl]anthracene, 1,5-bis [2-(N,N-diethylamino)acetyl]anthracene, 1,5-bis[5-(N-ethyl-N-propylamino)valeryl]anthracene, 1,5-bis [2-(N-methyl-N-propylamino)acetyl]anthracene, 1,5-bis (6-morpholinohexanoyl)anthracene, 1,5-bis[3-ethyl-4-(N-ethyl-N-methylamino)butyryl]anthracene, 1,5-bis (3-piperidinopropionyl)anthracene, 1,5-bis{2-[N-butyl-N-(2,2-dimethylbutyl)amino[acetyl}anthracene, 1,5-bis[2,2-dimethyl-4-(N-methyl-N-pentylamino)butyryl]anthracene, 1,5-bis[5-(N,N-diallylamino)-3-methylvaleryl]anthracene, 1,5-bis(6-aminohexanoyl)anthracene, 1,5-bis [5-(N,N-dicyclopropylamino)valeryl]anthracene, 1,5-bis {2,2-dimethyl-3-[N,N-bis-(3-methylbutyl)amino]propionyl}anthracene, 1,5-bis(6-pyrrolidinylhexanoyl)anthracene and 1,5-bis[5-(N-methylamino)valeryl]anthracene.

Similarly, the compounds of the present invention includes structures in which R₃ represents a hydrogen atom in the 5-position of the anthracene nucleus and in which the 8-position of the anthracene nucleus contains the radical

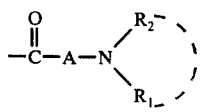

as more fully illustrated by the following general formula:

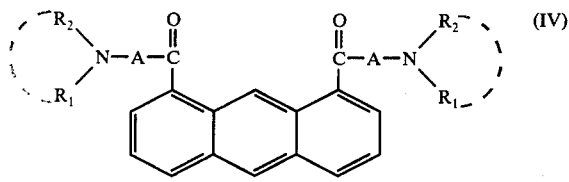 (IV)

wherein the symbols A, R₁ and R₂ have the aforementioned values. Illustrative of the base compounds of this invention represented by formula (IV) are: 1,8-bis [5-(N-butyl-N-propylamino)valeryl]anthracene, 1,8-bis [2-(N-ethyl-N-methylamino)acetyl]anthracene, 1,8-bis [6-(N-butylamino)hexanoyl]anthracene, 1,8-bis[3-(N,N-diethylamino)propionyl]anthracene, 1,8-bis{4-[N,N-bis(4-methylpentyl)amino]butyryl}anthracene, 1,8-bis {2-[N,N-bis(3-butenyl)amino]acetyl}anthracene, 1,8-bis(5-aminovaleryl)anthracene, 1,8-bis{2-[N,N-bis (2-propyl)amino]acetyl}anthracene, 1,8-bis(4-piperidinobutyryl)anthracene, 1,8-bis[2,3-dimethyl-4-(N,N-dicyclobutylamino)butyryl]anthracene, 1,8-bis[6-(N,N-diethylamino) hexanoyl]anthracene, 1,8-bis(3-pyrrolidinylpropionyl)anthracene and 1,8-bis(4-morpholinobutyryl)anthracene.

The expression pharmaceutically acceptable acid addition salts encompasses any non-toxic organic or inorganic acid addition salts of the base compounds represented by either formula (III) or (IV). Illustrative inorganic acids which form suitable salts include hydrochloric, hydrobromic, sulfuric and phosphoric acid as well as acid metal salts such as sodium monohydrogen orthophosphate and potassium hydrogen sulfate. Illustrative organic acids which form suitable salts include the mono, di and tricarboxylic aicds, for example, acetic, fumaric, malic, tartaric, citric, ascorbic, maleic, hydroxymaleic, benzoic, hydroxybenzoic, phenylacetic, cinnamic, salicylic, 2-phenoxybenzoic, and sulfonic acids such as methane sulfonic acid and 2-hydroxyethane sulfonic acid. Either the mono or the di-acid salts can be formed, and such salts can exist in either a hydrated or a substantially anhydrous form.

The bis(ω-haloalkanoyl)anthracenes (II), useful as starting materials for the preparation of the compounds of the present invention, are readily prepared via a Friedel-Crafts acylation of anthracene. Suitable acylating agents which can be employed include chloroacetyl chloride, bromoacetyl bromide, 3-chloropropionyl chloride, 4-chlorobutyryl chloride, 5-chlorovaleryl chloride, 5-chloro-4-methylvaleryl chloride and 5-chloro-3-methylvaleryl chloride.

The acylation reaction can be carried out using a variety of solvents and under catalysis with a variety of Lewis acids. The temperature and duration of the reaction may be varied to allow for optimum reaction conditions. A preferred procedure combines one equivalent of anthracene with 2.5 equivalents of the acylating agent using methylene chloride as a solvent, followed by the portionwise addition of aluminum chloride. The temperature of the reaction is maintained below 0° C with continuous stirring. Once the aluminum chloride addition is complete, the temperature is elevated to 25°-40° C for a period of from 12 to 36 hours. The reaction mixture is treated in the usual manner by decomposing the resulting complex in an ice water/hydrochloric acid mixture. The product so obtained can be recrystallized using a variety of solvents among which are methylene chloride and chloroform. This procedure can be varied to accommodate either a reverse addition of the acylating agent and Lewis acid or a reverse addition of the aromatic hydrocarbon and Lewis acid. The more reactive halogen derivatives, i.e., the bis(ω-iodoalkanoyl)anthracenes, can be prepared from their corresponding bis-chloro derivatives using a halogen exchange reaction under the conditions generally employed in the Conant-Finkelstein reaction.

Typical of the amines which have been found to be useful in the above reaction can be mentioned, for example, ammonia, or a compound which is a potential source of ammonia such as hexamethylenetetramine. Primary amines such as ethylamine and propylamine, and secondary amines such as diethylamine, dibutylamine, piperidine, morpholine and piperazine are successfully employed; the secondary amines representing the preferred group of amines.

The amination of bis(ω-haloalkanoyl)anthracenes (II) is carried out under a variety of conditions. For example, an anthracene halide may be heated together with a large excess of amine, with the excess amine serving as a reaction medium as well as a hydrohalide acceptor. This method is particularly suitable for readily available amines, the excess of which can be removed from the reaction mixture either by distillation under reduced pressure or by extraction of the reaction mixture and washing the extract with water. Alternatively, amination can take place by heating one equivalent of the anthracene with approximately four equivalents of the amine in a solvent medium using a variety of solvents as the reaction medium. Such solvents include aromatic solvents, as for example, benzene, toluene and xylene; ethers, such as tetrahydrofuran and dioxane; ketones such as acetone or butanone; aprotic solvents such as N,N-dimethylformamide, N,N-dimethylacetamide and dimethylsulfoxide; and aqueous or co-mixtures of these solvents.

When the halogen in formula (II) is chlorine, the reaction is frequently promoted by the addition of either sodium or potassium iodide, the iodide salt being used in either catalytic or stoichiometric amounts. In some instances, it may be advantageous to use only two equivalents of the amine for each equivalent of the bis(ω-haloalkanoyl)anthracene with an excess of an inorganic base such as powdered sodium or potassium carbonate being used as the hydrohalide acceptor. Normally, the reaction takes place anywhere from 30 minutes to 2 weeks at temperatures ranging from −30° to 150° C. When volatile amines are employed, the reaction is best carried out under pressure in a suitable pressure reactor or autoclave.

The 1,5 or 1,8-bis-basic acetyl ketones of anthracene are prepared from known 1,5 and 1,8-diacetylanthracenes. Such diacetylanthracenes are prepared by the Friedel-Crafts acetylation of anthracene as described by Gore et al, J. Chem. Soc., 1966, (C) 1729, or Buu-Hoï et al, J. Chem. Soc., 1968, (C) 2070. The diacetylanthracenes so prepared can be halogenated using cupric bromide and the resulting 1,5 or 1,8-bis(dihaloacetyl)anthracene aminated as previously described.

Alternatively, the amination reaction may be effected on a derivative of compound (II) such as a 1,5-bis-ethyleneketal derivative of 1,5-bis($\omega$-haloalkanoyl) anthracene. Such ketal derivatives are prepared by allowing a 1,5-bis($\omega$-haloalkanoyl)anthracene to react with ethylene glycol in the presence of p-toluenesulfonic acid. The resulting ketal is subsequently hydrolyzed and aminated as described to form the products of the present invention.

The compounds of formula (I) wherein A is an alkylene chain having from 3 to 6 carbon atoms can be prepared by the reaction of a Grignard reagent with an anthracene bis-ester or bis-amide as illustrated in the following general reaction:

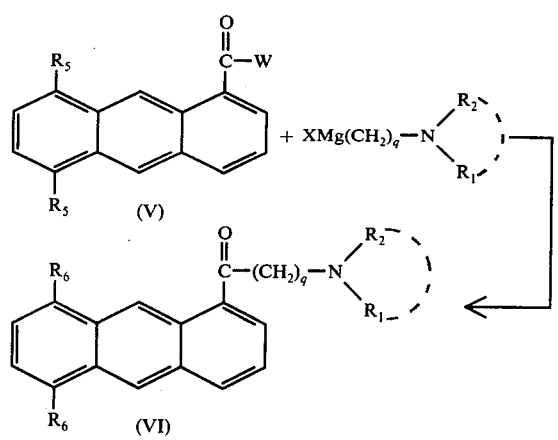

In the above reaction $R_5$ represents hydrogen or the group

with the proviso that one and only one such $R_5$ group is hydrogen; the symbol W represents the groups

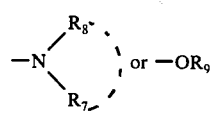

X represents bromine or chlorine; Q is an integer of from 3 to 6; the symbols $R_1$ and $R_2$ have the values previously assigned with the proviso that they cannot be hydrogen; and $R_6$ is either hydrogen or the group

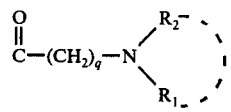

with the proviso that one and only one such $R_6$ group is hydrogen. As indicated above, the amides can, in addition, be further N-substituted so that the groups $R_7$ and $R_8$ represent either hydrogen or a lower alkyl group having from 1 to 6 carbon atoms. The esters which are used in the Grignard reaction are represented by the group

in which $R_9$ may be either a straight or a branched lower alkyl having from 1 to 6 carbon atoms or an aryl group such as phenyl or naphthyl.

The 1,5 and 1,8-bis-esters and bis-amides of anthracene used as starting materials for the Grignard reaction are known compounds and can be prepared from the corresponding anthracene dicarboxylic acids or dicyanoanthracenes using standard reaction procedures known to the art. The addition of the Grignard reagent to the 1,5 or 1,8-bis-esters and amides is generally conducted at low temperatures ranging from $-70°$ to $0°$ C. Once the addition has been completed, the reaction is maintained at a temperature ranging from $0°$ to $80°$ C. for a period of from 1 to 24 hours to ensure completion. The Grignard reagents can be prepared by reacting a solution of the aminoalkyl halide with magnesium utilizing standard procedures well known to the art, taking the usual precautions to eliminate moisture.

The compounds of formula (I) in which A is ethylene can be prepared via a Mannich reaction as illustrated in the following reaction scheme:

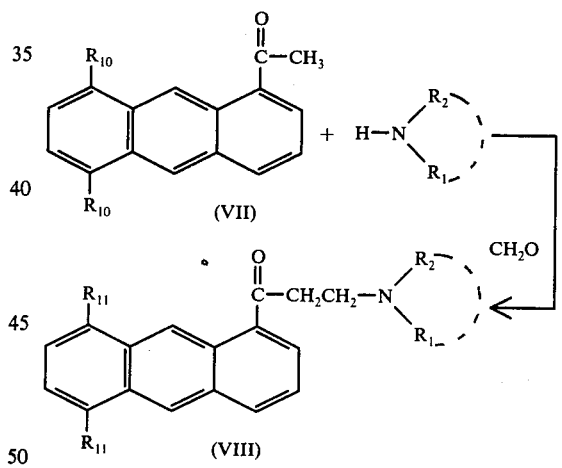

In the above reaction $R_{10}$ can be hydrogen or acetyl with the proviso that one and only one such $R_{10}$ group is hydrogen. Similarly, the group $R_{11}$ can be hydrogen or the group

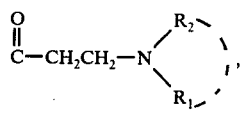

in which $R_1$ and $R_2$ have the values previously designated, with the proviso that one and only one such $R_{11}$ group is hydrogen. The Mannich reaction proceeds in from 1 to 24 hours in such solvents as water, acetic acid, ethanol, butanol, dioxane and tetrahydrofuran by combining one equivalent of the 1,5- or 1,8-diacetylanthracene with two or more equivalents of the particular amine employed in the presence of three or more equivalents of formaldehyde. In the above reaction, either of two sources of formaldehyde are employed. If an aqueous formalin solution is utilized as the source of formaldehyde, the reaction may be conducted as a suspension. Alternatively, a co-solvent such as methanol may be added in order to allow the reaction to proceed in a homogeneous medium. If the source of formaldehyde is paraformaldehyde, the reaction is conducted in the organic solvents previously described. Sometimes it is desirable to add a slight excess of hydrochloric acid to the reaction mixture in order to more readily promote the depolymerization of paraformaldehyde either during the reaction or upon the completion of the reaction. The secondary amine employed in this reaction is added to the reaction medium either as its hydrochloride salt or in the form of its free base. Typical of the secondary amines which may be utilized in the above reaction are dimethylamine, dibutylamine, piperidine, morpholine and piperazine.

The compounds of the present invention are antiviral agents. Preferably they are administered to an animal host to prevent or inhibit viral infections. The term host refers to any viable biological material or intact animal including humans which is capable of inducing the formation of interferon and which serves as a support means for virus replication. The host can be of animal or mammalian origin. Illustratively such hosts include birds, mice, rats, guinea pigs, gerbils, ferrets, dogs, cats, cows, horses and humans. Other viable biological material such as used in the production of vaccines may also act as a host. Thus, tissue cultures prepared from organ tissues, such as mammalian kidney or lung tissue, as well as tissue cultures prepared from embryo tissue, such as obtained from amniotic cells or chick allantoic fluid, have been found to be useful hosts.

The treatment of virus infections for purposes of the present invention encompasses both the prevention and the inhibition of characteristic disease symptoms in a mammalian host susceptible to invasion by a pathogenic virus. Illustrative of mammalian virus infections which can be prevented or inhibited by the administration of the compounds of the present invention are infections caused by picornaviruses, such as encephalomyocarditis virus; myxoviruses, such as influenza $A_2$ (Jap/305) virus; arboviruses, such as Semliki forest virus; the herpes group of viruses, including herpes simplex; and the poxviruses, as for example vaccinia IHD. Thus, for example, the compounds of the present invention when administered orally or subcutaneously to mice in varying doses either shortly prior or subsequent to a fatal inoculation of a neurotropic virus such as encephalomyocarditis virus, having a $LD_{50}$ anywhere from 5 to 50, delay or prevent completely the onset of death. Salts of these compounds are generally administered in compositions containing a 0.15% aqueous hydroxyethylcellulose vehicle, whereas the free base compounds are generally administered in compositions containing a 10% aqueous surfactant vehicle in order to help solubilize the compound. In general, ten mice are used for each treated group with an additional 20 mice serving as a control group. At the time of administration the test virus is titrated in order to determine the potency or $LD_{50}$ for the particular virus pool used as a challenge. The control animals are given a placebo containing the identical volume of vehicle without, of course, the active ingredient. Because of the lethal nature of the test system employed, the antiviral nature of the test compound is dramatically illustrated by a side by side comparison of the survival time of treated animals with the untreated control group of animals.

Respiratory viruses, such as influenza $A_2$ (Jap/305) virus, which are also lethal to the test animals employed, are administered via intranasal instillation. Animals infected in this manner have the active ingredients administered in the same manner as the test virus, and again a side by side comparison is made of the survivors of the animals treated with the untreated control animals.

Inexplicably, a mouse fatally infected with encephalomyocarditis or influenza virus occasionally survives without further treatment. This may be the result of a prior, interferon-induced infection in the mouse, or perhaps due to some genetic factor or other natural defense mechanism not presently understood. For this reason the control group selected is of sufficient size as to statistically reduce to a negligible amount the influence of such a chance survivor upon the test results.

The vaccinia test virus is typical of the dermatotrophic type viruses which respond to treatment with compositions containing the compounds of the instant invention. The vaccinia virus generally produces a nonfatal infection in mice, producing characteristic tail lesions when the virus is subcutaneously administered to the tail of the mouse. The instant compounds are administered either orally or subcutaneously either prior to or subsequent to the vaccinia infection. Tail lesions are subjectively scored on the eighth day following infection against untreated animals which serve as a control group. The compounds of the present invention have been found to be effective in varying degrees against one or all of these test virus systems.

The mode of activity of the active ingredients of the present invention is not rigorously defined. Inter alia, the compounds of the present invention may induce the formation of interferon in a viable host. Interferon is a biological substance of unknown chemical structure, presumably proteinaceous in nature, which is produced by host cells in response to a viral infection. The interferon so produced acts to induce a virus inhibiting substance, which inhibits in some yet unknown manner the intracellular replication of the virus without appearing to have any inactivation effect per se upon the virus itself. A few of the viruses susceptible to interferon replication inhibition are described in Horsfall and Tamm, "Viral and Rickettsial Infections of Man", 4th Edition (1965), J. B. Lippincott Company, pp. 328-9.

As previously indicated, the compounds of the present invention may be prophylactically administered in order to prevent the spread of contagious viral diseases or they may be therapeutically administered to a host already infected intended for their curative effect. When administered prophylactically, it is preferred that the administration be made within 0 to 96 hours prior to the infection of the host animal with a pathogenic virus. When the compounds of the present invention are administered for their curative effect, it is preferred that they are administered within about 1 or 2 days following infection of the host in order to obtain the maximum therapeutic effect.

The dosage to be administered will be dependent upon such parameters as the particular virus for which either treatment or prophylaxis is desired, the species of animal involved, its age, health, weight, the extent of infection, concurrent treatment, if any, frequency of treatment and the nature of the effect desired. A daily dose of the active ingredients will generally range from about 0.1 mg to about 500 mg per kg of body weight. Illustratively, dosage levels of the administered active ingredients for intravenous treatment range from about 0.1 mg to about 10 mg per kg of body weight; for intraperitoneal administration range from about 0.1 mg to about 50 mg per kg of body weight; for subcutaneous administration range from about 0.1 mg to about 250 mg per kg of body weight; for oral administration may be from about 0.1 mg to about 500 mg per kg of body weight; for intranasal instillation range from about 0.1 mg to about 10 mg per kg of body weight; and for aerosol inhalation therapy, the range is generally from about 0.1 mg to about 10 mg per kg of body weight.

The novel compounds described herein can also be administered in various different dosage unit forms, e.g., oral compositions such as tablets, capsules, dragees, lozenges, elixirs, emulsions, clear liquid solutions and suspensions; parenteral compositions such as intramuscular, intravenous or intradermal preparations; and topical compositions, such as lotions, creams or ointments. The amount of active ingredient contained in each dosage unit form will, of course, vary widely according to the particular dosage unit employed, the animal host being treated, and the nature of the treatment, i.e., whether prophylactic or therapeutic in nature. Thus, a particular dosage unit may contain from about 2.0 mg to over 3.0 g of active ingredient in addition to the pharmaceutical excipients contained therein.

The novel compounds described herein can be employed in conjunction or admixture with additional organic or inorganic pharmaceutical excipients. Suitable solid excipients include gelatin, lactose, starches, magnesium stearate and petrolatum. Suitable liquid excipients include water and alcohols such as ethanol, benzyl alcohol and the polyethylene alcohols either with or without the addition of a surfactant. In general, the preferred liquid excipients particularly for injectable preparations, include water, saline solution, dextrose and glycol solutions such as an aqueous propylene glycol or an aqueous solution of polyethylene glycol. Liquid preparations to be used as sterile injectable solutions will ordinarily contain from about 0.5% to about 25% by weight, and preferably from about 1% to about 10% by weight, of the active ingredient in solution. In certain topical and parenteral preparations, various oils are utilized as carriers or excipients. Illustrative of such oils are mineral oils, glyceride oils such as lard oil, cod liver oil, peanut oil, sesame oil, corn oil and soybean oil.

A preferred method of administration for the compounds of the present invention is orally either in a solid dose form such as a tablet or capsule, or in a liquid dose form such as an elixir, suspension, emulsion or syrup. Ordinarily the active ingredient comprises from about 0.5% to about 10% by weight in an oral liquid composition. In such compositions, the pharmaceutical carrier is generally aqueous in nature, as for example, aromatic water, a sugar-based syrup or a pharmaceutical mucilage. For insoluble compounds suspending agents may be added as well as agents to control viscosity, as for example, magnesium aluminum silicate or carboxymethylcellulose. Buffers, preservatives, emulsifying agents and other excipients can also be added.

For parenteral administration such as intramuscular, intravenous or subcutaneous administration, the proportion of active ingredient ranges from about 0.05% to about 20% by weight, and preferably from about 0.1% to about 10% by weight of the liquid composition. In order to minimize or eliminate irritation at the site of injection, such compositions may contain a non-ionic surfactant having a hydrophile-lipophile balance (HLB) of from about 12 to about 17. The quantity of surfactant in such formulations ranges from about 5% to about 15% by weight. The surfactant can be a single component having the above identified HLB, or a mixture of two or more components having the desired HLB. Illustrative of surfactants useful in parenteral formulations are the class of polyoxyethylene sorbitan fatty acid esters as, for example, sorbitan monooleate and the high molecular weight adducts of ethylene oxide with a hydrophobic base, formed by the condensation of propylene oxide with propylene glycol. The concentration of active ingredient contained in these various parenteral dosage unit forms varies over a broad range and comprises anywhere from about 0.05% to about 20% by weight of the total formulation, the remaining component or components comprising excipients previously mentioned.

The active ingredients of the present invention can also be admixed directly with animal feeds or incorporated into the drinking water of animals. For most purposes, an amount of active ingredient is used which provides from about 0.0001% to about 0.1% and preferably, from about 0.001% to about 0.02% by weight of the active ingredient based upon the total weight of feed intake. The active ingredients can be admixed in animal feed concentrates, suitable for use by farmers or livestock growers for incorporation in appropriate amounts with the final animal feeds. These concentrates ordinarily comprise from about 0.5% to about 95% by weight of the active ingredient compounded with a finely divided solid carrier or flour, such as wheat, corn, soybean or cottonseed flour. Depending upon the particular animal to be fed, nutrients and fillers may also be added such as ground cereal, charcoal, fuller's earth, oyster shells and finely divided attapulgite or bentonite.

The active ingredients of the present invention can be packaged in a suitable pressurized container together with an aqueous or volatile propellant for use as an aerosol. A suitable discharge valve is fitted to an opening in the container from which the active ingredients may be conveniently dispensed in the form of a spray, liquid, ointment or foam. Additional adjuvants such as co-solvents, wetting agents and bactericides may be employed as necessary. Normally, the propellant used is a liquified gaseous compound, preferably a mixture of low molecular weight fluorinated hydrocarbons. These haloalkanes are preferred because of their compatibility with the active ingredients of the present invention, and because they are non-irritating when applied to skin surfaces. Other useful propellants include ethylene oxide, carbon dioxide, propane and nitrogen gas.

The invention described herein is more particularly illustrated by means of the following specific examples:

EXAMPLE I

1,5-Diacetylanthracene

To a solution of 85 g of aluminum chloride (0.615 mole) and 50 g of acetyl chloride (0.64 mole) contained in 600 ml of methylene chloride is added portionwise a slurry of 36 g of anthracene (0.21 mole) dissolved in 500 ml of methylene chloride. The mixture is heated at its reflux temperature for 3 hours, cooled in an ice bath and the excess reagent decomposed with ice. The reaction mixture is further diluted and the organic phase separated, dried and the volatile materials removed. The solid when crystallized from nitromethane yields 18.6 g of crude 1,5-diacetylanthracene, m.p. 185°–205° C (reported 212° C).

EXAMPLE II 1,5-Diacetylanthracene
1,8-Diacetylanthracene

To a solution of 140 ml of acetyl chloride in 2 liters of chloroform is added by portionwise addition 450 g of aluminum chloride. The mixture is stirred until a complete solution of aluminum chloride occurs, following which a suspension of 200 g of anthracene in 3 liters of methylene chloride is slowly added. The mixture is refluxed for 2 hours and allowed to come to room temperature with stirring for an additional 1 hour. The solid is filtered and the residue poured into an ice-water mixture forming a yellow precipitate. The precipitate is collected and dissolved in hot toluene. The toluene solution is dried, decolorized with charcoal and chilled to yield 150 g of a yellow solid consisting primarily of a mixture of 1,5- and 1,8-diacetylanthracene. Fractional crystallization of the mixture from acetic acid yields 45 g of pure 1,5-diacetylanthracene, m.p. 208°–210° C. Evaporation of the mother liquor gives a crude solid which is fractionally crystallized from dimethylformamide, chloroform and nitromethane, respectively. From the nitromethane solution is obtained 24 g of 1,8-diacetylanthracene, m.p. 178°–181° C.

EXAMPLE III 1,5-Bis(bromoacetyl)anthracene

A mixture of 50 g of 1,5 diacetylanthracene (0.19 mole), 170 g of cupric bromide (0.76 mole), 500 ml of ethyl acetate and 500 ml of chloroform is refluxed for a period of 16 hours. The insoluble material is filtered and extracted with hot dimethylformamide. The dimethylformamide extract yields a crude product which when recrystallized from nitromethane yields 27.2 g of 1,5-bis(bromoacetyl)anthracene having a m.p. 215° C. The chilled reaction filtrate yields an additional 8.5 g of crude product.

Following essentially the same procedure but substituting 1,8-diacetylanthracene for the 1,5-isomer above, the desired 1,8-bis(bromoacetyl)anthracene is obtained.

EXAMPLE IV 1,5-Bis(diethylaminoacetyl)anthracene dihydrobromide hemihydrate

A solution of 18.2 g of 1,5-bis(bromoacetyl)anthracene, (0.042 mole) and 12.5 g of diethylamine (0.17 mole) in 1.6 liters of benzene is refluxed for 2.5 hours. On cooling, excess saturated ethereal hydrobromic acid is added to precipitate the product as the dihydrobromide hemihydrate. Recrystallization of this salt from 200 ml of methanol yields 12 g of 1,5-bis(diethylaminoacetyl)anthracene dihydrobromide hemihydrate, m.p. 285°–6° C.

Replacing the diethylamine with an appropriate amount of the following secondary amines: N-methyl-N-propylamine, N-hexyl-N-ethylamine, N,N-dihexylamine, N-butyl-N-(2-methyl-2-propyl)amine, N-pentyl-N-propylamine, morpholine and piperidine, and using essentially the same procedure described above, the following products are respectively prepared: 1,5-bis[2-(N-methyl-N-propylamino)acetyl]anthracene, 1,5-bis[2-(N-hexyl-N-ethylamino)acetyl]anthracene, 1,5-bis[2-(N,N-dihexylamino)acetyl]anthracene, 1,5-bis{2-[N-butyl-N(2-methyl-2-propyl)amino]acetyl}anthracene, 1,5-bis[2-(N-pentyl-N-propylamino)acetyl]anthracene, 1,5-bis(2-morpholinoacetyl)anthracene and 1,5-bis(2-piperidinoacetyl)anthracene.

Substituting an equal amount of 1,8-bis(bromoacetyl)anthracene for the 1,5-bis(bromoacetyl)anthracene in the above example results in the formation of the corresponding 1,8-bis(diethylaminoacetyl)anthracene dihydrobromide.

EXAMPLE V 1,5-Bis(5-chlorovaleryl)anthracene

To a mixture of 226 g of aluminum chloride (0.17 mole), 280 g of 5-chlorovaleryl chloride (1.18 mole), and 5 liters of methylene chloride is added 100 g (0.56 mole) of anthracene contained in 1 liter of methylene chloride. The mixture is stirred for 1.5 hours and added to 2 liters of an ice-water mixture. The organic layer is separated and stirred with 2 liters of a saturated aqueous sodium bicarbonate solution for 16 hours. The organic phase is separated, dried and evaporated in vacuo to give a residue, which when crystallized from benzene yields 69 g of the desired product, 1,5-bis(5-chlorovaleryl)anthracene. Recrystallization from ethyl cellosolve and again from benzene results in a product having bright yellow needles and having a m.p. of 146°–8° C.

Following essentially the same procedure but replacing the 5-chlorovaleryl chloride above with an appropriate equivalent amount of 4-chlorobutyryl chloride, 6-chlorohexanoyl chloride, 4-chloro-2-methylbutyryl chloride, 5-chloro-3-methylvaleryl chloride, 4-chloro-2,3-dimethylbutyryl chloride and 4-chloro-3-methylvaleryl chloride results in the preparation of the following 1,5-bis($\omega$-haloalkanoyl)anthracenes, respectively: 1,5-bis(4-chlorobutyryl)anthracene, 1,5-bis(6-chlorohexanoyl)anthracene, 1,5-bis(4-chloro-2-methylbutyryl)anthracene, 1,5-bis(5-chloro-3-methylvaleryl)anthracene, 1,5-bis(4-chloro-2,3-dimethylbutyryl)anthracene and 1,5-bis(4-chloro-3-methylvaleryl)anthracene.

EXAMPLE VI 1,5-Bis(5-diethylaminovaleryl)anthracene

In each of four Carius tubes is placed 10 g of 1,5-bis(5-chlorovaleryl)anthracene (0.024 mole), 80 ml of diethylamine and 40 ml of tetrahydrofuran. The tubes are heated to 110° C. for 30 hours, cooled and their contents combined. The volatile components are evaporated in vacuo and the residue is slurried with 400 ml of chloroform. The organic phase is extracted twice with 100 ml portions of water, and two additional times with 100 ml portions of 10% HCl solution. The combined acid extracts are neutrallized using a cold 50% sodium hydroxide solution and reextracted with two 100 ml portions of chloroform. The combined chloroform extracts are dried over magnesium sulfate, filtered, evaporated to dryness and the residue is crystallized from n-heptane to give 36 g of 1,5-bis(5-diethylaminovaleryl)anthracene having a m.p. of 65°–7° C.

Replacing the 1,5-bis(5-chlorovaleryl)anthracene with an equimolecular amount of the corresponding 1,8-isomer results in the preparation of 1,8-bis(5-diethylaminovaleryl)anthracene.

EXAMPLE VII

1,5-Bis(4-chlorobutyryl)lanthracene-bis-ethyleneketal

A solution of 39 g of 1,5-bis(4-chlorobutyryl)anthracene (0.1 mole) prepared in accordance with the procedure of Example V, 20 ml of ethylene glycol (0.36 mole), 3 g of p-toluenesulfonic acid and 1.5 liters of benzene is refluxed for 96 hours using a Dean-Stark water separator. The solvent is evaporated in vacuo and the residue is crystallized from acetonitrile. Recrystallization from ethyl acetate results in the preparation of 25.5 g of 1,5-bis(4-chlorobutyryl)anthracene-bis-ethyleneketal having a m.p. of 150°–3° C.

EXAMPLE VIII

1,5-Bis(4-diethylaminobutyryl)anthracene dihydrochloride

In each of four Carius tubes is placed 7.8 g of 1,5-bis(4-chlorobutyryl)anthracene-bis-ethylene ketal (0.015 mole), prepared in accordance with the preceeding example, 100 ml of diethylamine, and 50 ml of tetrahydrofuran. The tubes are heated to 140° C. for 48 hours, cooled, their contents combined and the volatile components evaporated in vacuo. The residue is dissolved in 400 ml of chloroform, washed with water and the chloroform solution is extracted twice with 100 ml portions of a 20% HCl solution. The aqueous acid extracts are combined, neutralized with a cold 50% sodium hydroxide solution and re-extracted with two 100 ml portions of chloroform. The chloroform extracts are combined, dried and the solvent removed in vacuo. The residue so obtained is dissolved in ether, cooled and treated with an excess of a saturated ethereal hydrochloric acid solution. The gummy residue which forms is separated and crystallized once from acetonitrile and recrystallized two additional times from absolute alcohol to give 18 g of the desired product, 1,5-bis(4-diethylaminobutyryl)anthracene as its dihydrochloride salt having a m.p. of 247°–9° C.

EXAMPLE IX

The following Example is illustrative of the antiviral activity for the compounds of the present invention.

Thirty mice weighing approximately 20 gms each are divided into two groups, a control group of 20 animals and a test group of 10 animals. All of the animals are challenged with a fatal dose ($12LD_{50}$) of encephalomyocarditis virus. The test group of animals are tested both prophylactically and therapeutically using a parenteral composition containing 1,5-bis[2-(diethylamino)acetyl]anthracene dihydrobromide as the active ingredient dissolved in a solution of a 0.15% aqueous hydroxyethylcellulose solution as the vehicle. The composition contains the active ingredient in an amount such that eachdosage contains 0.25 ml which is equivalent to a dose level of 50 mg per kg. The control group receives a subcutaneous placebo containing the same volume of vehicle without the active ingredient. Observations over a 10 day period show the termination of all of the control animals within a period of from 4 to 5 days, with the treated group surviving for a substantially longer period of time.

EXAMPLE X

Preparation of a capsule formulation

An illustrative composition for hard gelatin capsules is as follows:

|     |                                                       | Per Capsule |
| --- | ----------------------------------------------------- | ----------- |
| (a) | 1,5-bis(4-diethylaminobutyrl)anthracene dihydrochloride | 200 mg      |
| (b) | Talc                                                  | 35 mg       |

The formulation is prepared by passing the dry powders

The formulation is prepared by passing the dry powders of both (a) and (b) through a fine mesh screen and mixing them well. The powder is then filled into No. 0 hard gelatin capsules at a net fill of 235 mg per capsule.

In a similar fashion, a soft gelatin capsule is prepared in which the talc is omitted. The dry 1,5-bis(4-diethylaminobutyryl)anthracene dihydrochloride powder can be filled directly as a granulation, slug or compressed tablet into a rotary dye or plate mold in which the soft gelatin capsule is formed.

EXAMPLE XI

Preparation of a tablet formulation

An illustrative composition for tablets is as follows:

|     |                                                        | Per Tablet |
| --- | ------------------------------------------------------ | ---------- |
| (a) | 1,5-bis(5-diethylaminovaleryl)anthracene dihydrochloride | 100 mg     |
| (b) | Wheat starch and starch paste                          | 15 mg      |
| (c) | Lactose                                                | 33.5 mg    |
| (d) | Magnesium stearate                                     | 1.5 mg     |

The granulation obtained upon mixing lactose, starch and granulated starch paste is dried, screened and mixed with the active ingredient and magnesium stearate. The mixture is compressed into tablets weighing 150 milligrams each.

EXAMPLE XII

Preparation of an oral syrup formulation

A 2% weight per volume syrup of 1,5-bis(2-diethylaminoacetyl)anthracene dihydrochloride hemihydrate is prepared by the usual pharmaceutical techniques in accordance with the following formula:

|     |                                                                                 | Grams |
| --- | ------------------------------------------------------------------------------- | ----- |
| (a) | Finely divided 1,5-bis(2-diethylaminoacetyl)anthracene dihydrochloride hemihydrate | 2.0   |
| (b) | Sucrose                                                                         | 33.3  |
| (c) | Chloroform                                                                      | 0.25  |
| (d) | Sodium Benzoate                                                                 | 0.4   |
| (e) | Methyl p-hydroxybenzoate                                                        | 0.02  |
| (f) | Vanillin                                                                        | 0.04  |
| (g) | Glycerol                                                                        | 1.5   |
| (h) | Purified water to 100.0 ml                                                      |       |

EXAMPLE XIII

Preparation of parenteral formulation

An illustrative composition for a parenteral injection is the following emulsion:

| Each ml Contains | Ingredients | Amount |
|---|---|---|
| 50 mg | 1,5-bis(4-diethylamino-butyrl)anthracene dihydrochloride | 1.000 g |
| 100 mg | Polyoxyethylene sorbitan monooleate | 2.000 g |
| 0.0064 | Sodium chloride | 0.128 g |
| | Water for injection, q.s. | 20.000 ml |

The parenteral composition is prepared by dissolving 0.64 g of sodium chloride in 100 ml of water for injection, mixing the polyoxyethylene sorbitan monooleate with the 1,5-bis(4-diethylaminobutyryl)anthracene dihydrochloride, adding a sufficient solution of the sodium chloride in water to the active ingredient and polyoxyethylene sorbitan monooleate to bring the volume to 20 ml, shaking the mixture, and finally autoclaving the mixture for 20 minutes at 110° C., at 15 p.s.i.g. steam pressure. The composition can be dispensed either in a single ampule for subsequent use in multiple dosages or in groups of 10 and 20 ampules for a single dosage administration.

EXAMPLE XIV

Preparation of dusting powder formulation

The following formulation illustrates a dusting powder for topical use:

| | | Per Kilogram |
|---|---|---|
| (a) | 1,5-bis(5-diethylaminovaleryl) anthracene | 10 gm |
| (b) | Silica aerogel | 980 gm |

The dusting powder is prepared by intimately blending the ingredients. The resulting mixture is then packaged in suitable dispensing containers.

We claim:

1. A bis-basic ketone of anthracene having the general formula:

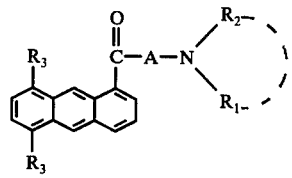

wherein A is a straight or branched alkylene chain having from 1 to 6 carbon atoms; $R_1$ and $R_2$ are each selected from the group consisting of hydrogen, lower alkyl having from 1 to 6 carbon atoms, cycloalkyl having from 3 to 6 carbon atoms, alkenyl having from 3 to 6 carbon atoms in which the unsaturation is in a position other than the 1-position of the alkenyl group, and when $R_1$ and $R_2$ are taken together with the nitrogen atom to which they are attached, represent the pyrrolidinyl, piperidino or morpholino radical; $R_3$ is selected from the group consisting of hydrogen and the radical

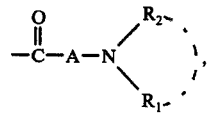

with the proviso that one and only one such $R_3$ group is hydrogen; and the pharmaceutically acceptable acid addition salts thereof.

2. A compound according to claim 1 having the formula:

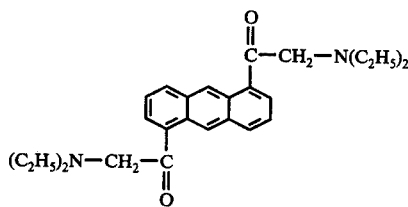

3. A compound according to claim 1 having the formula:

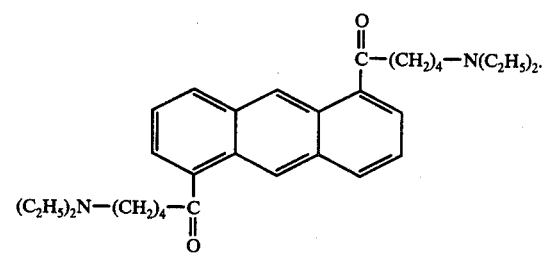

4. A compound according to claim 1 having the formula:

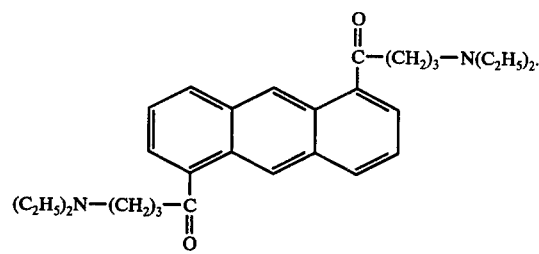

5. A compound of claim 1 wherein each $R_1$ and $R_2$ is a lower alkyl group having from 1 to 6 carbon atoms.

* * * * *